United States Patent [19]

Stammer

[11] 4,350,628
[45] Sep. 21, 1982

[54] PREPARATION OF DEHYDROPEPTIDES

[75] Inventor: Charles H. Stammer, Athens, Ga.

[73] Assignee: Research Corporation, New York, N.Y.

[21] Appl. No.: 247,006

[22] Filed: Mar. 24, 1981

Related U.S. Application Data

[62] Division of Ser. No. 80,210, Oct. 1, 1979, Pat. No. 4,283,328, which is a division of Ser. No. 921,239, Jul. 3, 1978, abandoned.

[51] Int. Cl.³ .................... C07C 103/52; C09B 23/00
[52] U.S. Cl. ............................ 260/112.5 R; 542/442; 542/443; 548/228
[58] Field of Search ................ 542/442, 443; 548/228; 260/112.5 R

[56] References Cited

U.S. PATENT DOCUMENTS

| | | | |
|---|---|---|---|
| 3,449,329 | 6/1969 | Wilde' | 542/443 |
| 3,466,315 | 9/1969 | Firestone et al. | 548/228 |
| 4,005,127 | 1/1977 | Knowles et al. | 542/442 |
| 4,285,935 | 8/1981 | Etschenberg et al. | 260/112.5 R |

OTHER PUBLICATIONS

Benoiton, et al., Journal Chem. Soc., (1964), 824–836.
Weiner, et al., J.A.C.S. 88, (1966), 3851–3859.
Patchornit, et al., J.A.C.S. 86, 1860–1861, (1964).
Riordan, et al., Tetrahedron Letter, (1976), 1247–1250.

Primary Examiner—Delbert R. Phillips
Attorney, Agent, or Firm—Oblon, Fisher, Spivak, McClelland & Maier

[57] ABSTRACT

A preparation of azlactones represented by the formula

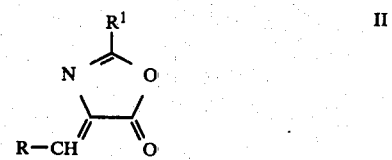

wherein R is a substituted or unsubstituted alkyl, aryl or nitrogen containing heterocyclic group, and $R^1$ is an N-blocked amino acid residue or peptide chain, and stereoisomers thereof, by oxidizing the corresponding saturated azlactone with a benzoquinone oxidizing agent in the presence of a base is disclosed. The unsaturated azlactones, some of which are novel, can be converted to dehydro peptides, which are useful as intermediates for preparing novel biologically active compounds, or themselves have biological activity.

10 Claims, No Drawings

PREPARATION OF DEHYDROPEPTIDES

The invention described herein was made in the course of work under a grant or award from the Department of Health, Education and Welfare.

This is a divisional of application Ser. No. 080,210, filed Oct. 1, 1979, now U.S. Pat. No. 4,283,328, which in turn is a division of application Ser. No. 921,239, filed July 3, 1978, now abandoned.

BACKGROUND OF THE INVENTION

In recent years peptide hormones and regulators of bodily functions have been discovered, e.g., bradykinin, enkephalin, TRH and LH-RH. In addition, other peptides having valuable properties have been discovered, e.g., aspartame.

In an effort to improve the activity and properties of these peptides, particularly the propensity to enzyme cleavage, extensive research has been conducted. One of the approaches taken has been to attempt to introduce a dehydro amino acid into the peptide sequence without adversely affecting the biological properties and optical activity of the compounds. Since most amino acids and peptides are optically active and only one stereoisomer has the desired biological properties, a sought after means to produce dehydropeptides is one that does not racemize the compound. This has been difficult to accomplish since processes which result in dehydro amino acids and dehydropeptides usually are conducted under conditions which result in an undesirable extent of racemization.

There is thus a need for a facile synthesis of optically active dehydropeptides having desirable biological properties and stability to enzyme cleavege.

PRIOR ART

Previous methods of producing dehydropeptides have generally been deficient since the processes result in low yields, are difficult to carry out, are more limited as to the compounds which can be produced, or result in racemized compounds.

Riordan et al., J. Org. Chem. 42,236–240 (1977) discloses the reaction of N-phtaloylglycl-D,L-phenylalanine and o-chloranil in acetic anhydride to produce an unsaturated azlactone which is converted to an unsaturated N-phthaloyl amino acid ester by ethanolysis.

Carter et al., Org. Reac. 3,198 (1947) and other reviewers of the chemistry of azlactones and unsaturated azlactones discuss a process wherein an azlactone is prepared in acetic anhydride from an N-acyl glycine and condensed with an alkyl or aryl aldehyde in basic medium to form the unsaturated azlactone which is then hydrolyzed to form an N-blocked dehydro amino acid which cannot be directly converted into a dehydropeptide.

Schmidt et al., Angew. Chem. Int. Ed. 16,327 (1977) and Ber. 108,2547 (1975) as well as Shin et al., Bull. Chem. Soc. Japan 43,3219 (1970) and 44,1657 (1971) disclose syntheses of dehydro amino acids which lead to dehydro amino acid esters which are difficult to convert to a dehydroprotein.

Olsen et al., J. Org. Chem. 42,2253,2256 (1977) and Rich et al., J. Org. Chem. 42,3815 (1977) have produced dehydropeptides directly from peptides. Olsen et al. require the presence of a leaving group in the percursor peptide which is eliminated on treatment with a base. The leaving group is derived from the sulfur atom of cysteine or the hydroxyl group of serine, threonine or phenylserine.

Rich et al. use a mercaptan to protect the double bond of an N-blocked dehydro amino acid. After the peptide is formed the mercaptan group is removed by oxidation and pyrolysis. This approach is disadvantageous since it has a multiplicity of steps and double bond cis and trans isomers are frequently formed.

Doherty et al., J. Biol. Chem. 147,617 (1943) produce unsaturated azlactones by the so-called "Bergmann method" which involves spontaneous dehydration of beta hydroxy amino acid azlactones to introduce double bonds.

Erlenmeyer, Ann. 275 (1893) and Plöchl, Ber. 170,1616 (1884) form unsaturated azlactones by reacting carbonyl compounds with acylglycines in the presence of acetic anhydride.

King, U.S. Pat. No. 2,478,661, Cook et al., U.S. Pat. No. 2,569,801 and Weitnauer, U.S. Pat. No. 2,782,203, disclose the preparation of azlactones with an unsaturated side chain by reacting amino acid compounds with acid anhydrides alone or in combination with a base such as pyridine or collidine.

Morin et al., C.A. 79,92072 g (1973) prepare dehydropeptides by oxidizing unsaturated azlactones with heavy metal acetates.

Link, S. G. PhD. dissertation #77-18065 University of Michigan (1977) reported making dehydroenkephalin; i.e. tyrosylglycyl-glycyl-dehydrophenylalanyl methionine amide using a dehydro dipeptide produced by the Bergmann method.

SUMMARY OF THE INVENTION

This invention relates to a process for preparing azlactones which have an unsaturated side chain. These azlactones, some of which are novel, are derived from peptides and are useful as intermediates for the preparation of dehydropeptides, some of which are novel, containing at least two amino acid residues.

The dehydropeptides produced according to this invention are generally characterized as being more resistant to enzyme degradation than the corresponding saturated peptide, more fat soluble than the corresponding saturated peptide, and having biological activity where the corresponding saturated peptide has biological activity.

The azlactones with the unsaturated side chain are prepared by dehydrogenating the side chain of an azlactone formed from an N-blocked peptide, preferably dipeptide, by reacting the azlactone with a benzoquinone oxidizing agent under alkaline conditions to introduce unsaturation at the alpha carbon atom, then converting the unsaturated azlactone to a dehydropeptide.

DETAILED DESCRIPTION OF THE INVENTION

The process of this invention is carried out by reacting an azlactone represented by the formula:

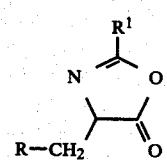

wherein R is a substituted or unsubstituted alkyl, aryl, or nitrogen containing heterocyclic group, and R¹ is an N-blocked amino acid residue or peptide chain, and stereoisomers thereof under basic conditions, with a quinone oxidizing agent to produce an azlactone with an unsaturated side chain represented by the formula:

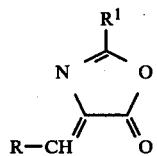

wherein R and R¹ have the same meanings as in Formula I, and stereoisomers thereof.

As used herein alkyl means straight or branched chain alkyl groups having from one to eight carbon atoms, e.g., methyl, ethyl, propyl, isopropyl, butyl, tertiary butyl, pentyl, hexyl, heptyl, octyl and the like; aryl means phenyl or naphthyl; and heterocyclic means a 5-membered ring containing at least one nitrogen atom and at least three carbon atoms or a 5-membered heterocyclic ring containing one nitrogen and 4 carbon atoms fused to a benzene ring; the substituents on the alkyl are hydroxyl, methylthio, guanidino, and amino; the substituents on the aryl are hydroxyl, iodo and phenoxy, the substituent on the heterocyclic is hydroxyl. Formulas I and II include all stereoisomers and racemic mixtures of the compounds.

This oxidation reaction can be depicted as follows:

REACTION SCHEME I

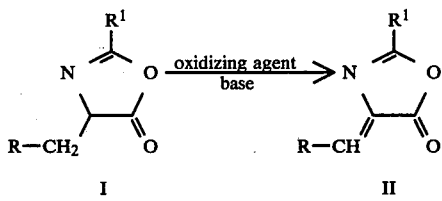

The azlactones which are used as starting materials in the process of this invention can be prepared by cyclizing N-blocked peptides, preferably dipeptides, using known cyclization methods; e.g., the mixed anhydride, acid halide or the carbodiimide method. Preferred for use in this invention is the use of carbodiimides.

When utilizing compounds represented by Formula I to form compounds represented by Formula II, stereoisomers and racemic mixtures of the starting compounds give rise to the corresponding stereoisomers or racemic mixtures of the final product.

The preferred N-blocked dipeptides can be any pair of amino acids or can be two of the same amino acid. Longer chain peptides can be used also. The peptides are optically active and can be in the racemic or the D or L forms. The choice of peptide depends on the dehydropeptide to be made. In every case the amino acid of the carboxyl terminal of the preferred dipeptide is the one which is dehydrogenated by the process of this invention.

The amino acids which can be at the N-blocked terminal of the peptide are, for example, glycine, serine, alanine, valine, norleucine, leucine, isoleucine, threonine, cysteine, cystine, methionine, arginine, lysine, ornithine, aspartic acid, glutamic acid, hydroxy glutamic acid, phenylalanine, phenylserine, tyrosine, 3,5-diiodotyrosine, thyroxine, tryptophan, proline, hydroxyproline, histidine and the like.

The group which blocks the terminal nitrogen on the peptide must be one that is stable to weak bases, e.g., bases having a pK in a range of about 6 to 8. These blocking groups are known to peptide chemists. Examples of such groups are benzoxycarbonyl, tertiary butoxy carbonyl, biphenyloxy carbonyl, phthaloyl and the like.

The amino acids which can be at the carboxyl terminal of the peptide are phenylalanine, tyrosine, tryptophan, and histidine.

The preferred oxidation agent to dehydrogenate the azlactone of Formula I according to this invention is 2,3-dichloro-5,6-dicyano-para-benzoquinone (DDQ). It has been found that while other benzoquinones, e.g., ortho-chloranil, para-chloranil and biphenylquinones can also cause dehydrogenation of azlactones according to this invention, they do not provide as high a yield as DDQ under the same conditions.

About 5 to 10% lower yields than obtained with the process of this invention are obtained when the above mentioned Riordan et al method of oxidizing in the presence of acetic anhydride is used.

The method of this invention requires the use of a basic catalyst. The base must be a weak base which is not strong enough to remove the N-blocking group, racemize the peptide, or otherwise interfere with the reaction. If the base is too strong, the yields are adversely affected. Bases which are suitable for use in this invention are weakly basic tertiary amines with pK's of about 6 to 8, e.g., collidine, pyridine, and imidazole. Preferred for use in the process of this invention is collidine.

The solvents suitable for use in the process of this invention are organic solvents, such as dimethoxyethane, ethyl acetate and the like. 1,2-Dimethoxyethane is the preferred solvent.

The relative amounts of reactants used in the process can vary widely. Generally about one mole of the azlactone per mole of oxidizing agent is used. However, this can vary from 0.5 to 1.5 mole of azlactone per mole of oxidizing agent. Also the relative amounts of the oxidizing agents and the base can vary from about 0.25 to 1.5 moles of base per mole of oxidizing agent. The preferred mole ratios are 1 mole of azlactone to 1 mole of oxidizing agent to 0.25 or 1 mole of base.

The oxidation reaction is normally completed within 24 hours at room temperature, e.g., about 25 to 30 degrees Celsius. While these time and temperature reaction parameters are not critical, yields are usually adversely affected if the reaction is allowed to continue beyond 48 hours. Higher or lower temperatures also adversely affect the yields. The following table illustrates the effect of the reaction conditions on the yields.

TABLE I

OXIDATION OF THE AZLACTONE OF N—CARBOBENZOXY GLYCYL-DL-PHENYLALNINE
(In DME Solvent)

| Oxidizing Agents | Base | Time (Hr) | Temperature °C. | Yield % |
|---|---|---|---|---|
| DDQ¹ | Collidine | 15 | 25–30 | 38 |
| DDQ¹ | Collidine | 24 | 25–30 | 48 |
| DDQ¹ | Collidine | 48 | 25–30 | 42 |
| DDQ¹ | Collidine | 72 | 25–30 | 39 |
| DDQ¹ | Collidine | 96 | 25–30 | 36 |
| DDQ¹ | Collidine | 120 | 25–30 | 34 |

TABLE I-continued
OXIDATION OF THE AZLACTONE OF N—CARBO-
BENZOXY GLYCYL-DL-PHENYLALNINE
(In DME Solvent)

| Oxidizing Agents | Base | Time (Hr) | Temperature °C. | Yield % |
|---|---|---|---|---|
| DDQ[1] | Pyridine | 24 | 25-30 | 43 |
| DDQ[1] | Imidazole | 24 | 25-30 | 46 |
| DDQ[1] | Imidazole | 36 | Reflux | 13 |
| DDQ[1] | 4-Dimethylamino Pyridine | 24 | 25-30 | 25 |
| DDQ[1] | Collidine | 24 | 25-30 | 48 |
| DDQ[1] | Collidine | 6/days | 5 | 17 |
| DDQ[2] | Collidine | 24 | 25-30 | 48 |
| O—Chloranil[1] | Collidine | 24 | 25-30 | 43 |
| P—Chloranil[1] | Collidine | 24 | 25-30 | <5 |
| P—Chloranil[1] | Collidine | 48 | 25-30 | 25 |
| Diethyl Azodicarboxylate[1] | Collidine | 24 | 25-30 | 11 |
| Ortho Chloranil[1] | Collidine | 24 | 25-30 | 43 |
| Ortho Chloranil[1] | Collidine | 48 | 25-30 | 36 |
| Ortho Chloranil[1] | Collidine | 72 | 25-30 | 35 |
| Ortho Chloranil[1] | Pyridine | 24 | 25-30 | 39 |
| Ortho Chloranil[1] | Imidazole | 24 | 25-30 | 33 |
| Ortho Chloranil[1] | Triethylamine | 24 | 25-30 | 17 |

The reaction is applicable to each stereoisomer or the racemate. To illustrate that the reaction does not cause racemization, the following reactions were carried out.

The azlactone of carbobenzoxy L-prolyl-dehydrophenylalanine was refluxed in tetrahydrofuran solution for 6 to 8 hours in the presence of pyridine, a weak base. No racemization occurred. The same azlactone was also refluxed in tetrahydrofuran in the presence of the strong base, triethylamine. Racemization occurred and was complete within 24 hours. This indicates that presence of the weak base in the process of this invention would not be expected to cause appreciable racemization of the optically active stereoisomers.

Racemization can be detected by NMR by treating both stereoisomers and the racemic unsaturated azlactone with (−)-alpha-phenethylamine in boiling ethyl acetate. The amides obtained from the optically active azlactones showed a sharp doublet for the methyl group in the NMR spectrum while the racemic compound gave an amide which showed a nicely separated pair of doublets corresponding to the expected diastereomers in the same region.

Novel compounds which can be made by the oxidation process of this invention are those represented by the following formula.

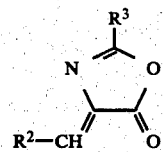

III wherein $R^2$ is a substituted or unsubstituted alkyl, aryl or nitrogen containing heterocyclic group and $R^3$ is an N-blocked amino acid residue or peptide chain and stereoisomers thereof.

Formula III is a general formula and it includes the racemic, the D and the L stereoisomers of the compounds within its scope.

Preferred compounds within Formula III as those wherein $R^2$ is phenyl and $R^3$ is N-blocked prolyl, N-blocked alanyl, N-blocked tyrosyl, N-blocked leucyl, N-blocked tryptophanyl, N-blocked aspartyl and N-blocked glutamyl. These compounds are preferred since they can be made into dehydropeptides that can be inserted into longer peptides to form compounds with useful activity. The most preferred novel compounds within formula III are those where $R^2$ is phenyl and $R_3$ is an N-blocked prolyl.

The unsaturated azlactones of Formulas II and III can be converted into N-blocked dehydropeptides having at least two amino acid residues and the corresponding dehydropeptides. The N-blocked dehydropeptides in some cases have valuable biological properties but in all cases they can be converted to dehydropeptides which either have valuable properties or can be inserted into a polypeptide to modify and improve its properties. The process of this invention thus provides a means to tailor-make dehydropeptides.

The unsaturated polypeptides or their N-blocked analogs which can be derived from the unsaturated azlactones of Formulas II and III according to this invention can contain up to fifteen amino acids including the dehydro amino acid. The identity of the amino acids in the polypeptide can vary depending on the particular polypeptide produced. All the amino acids found in biologically active polypeptides are contemplated. The dehydro amino acid can be anywhere in the polypeptide chain except at the N-terminal.

The polypeptides which can be made according to this invention are those represented by the following formula:

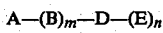

IV wherein A is an N-terminal amino acid in which the N can be blocked; B and E are independently one or more amino acids; and D is a dehydro amino acid selected from the group consisting of phenylalanine, tyrosine, tryptohan and histidine; m and n each are a whole number from 0 to 13 inclusive and the sum of m and n is from 0 to 13 inclusive; acid addition salts, lower alkyl esters and amides thereof; and stereoisomers thereof. Some of the compounds within Formula IV are novel and some are known. Those which are novel are represented by the following formula:

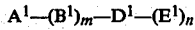

V wherein m and n are each a whole number from 0 to 13 inclusive and the sum of n and m is from 0 to 13 inclusive; $A^1$ is selected from the group consisting of N-blocked pyroglutamyl, pyroglutamyl, N-blocked aspartyl, aspartyl, N-blocked arginyl, 3-mercaptopropionyl arginyl, N-blocked prolyl, prolyl, 3-mercapto-2-methyl-propionyl N-blocked leucyl, Leucyl, N-blocked sarcosyl and sarcosyl; $B^1$ is selected from the group consisting of leucyl, alanyl, glycyl, prolyl, valyl, arginyl, and combinations thereof; $D^1$ is a dehydro amino acid selected from the group consisting of phenylalanine, tyrosine, tryptophan and histidine; $E^1$ is selected from the group consisting of phenylalanine, methionine, serine, proline, arginine, histidine, leucine, valine, isoleucine, threonine, alanine, and combinations thereof; acid addition salts, lower alkyl esters and amides thereof; and stereoisomers thereof.

The following are typical novel compounds of Formula IV which can be made according to this invention.
Pyroglutamyl-dehydrophenylalanine prolinamide;
Aspartyl-dehydrophenylalanine methyl ester;
Pyroglutamyl-dehydrophenylalanine;
Tyrosyl-D-alanyl-glycyl-dehydrophenylalanyl methionine amide;
Arginyl-prolyl-prolyl-glycyl-dehydrophenylalanyl-seryl-prolyl-phenylalanyl-arginine;
N-carbobenzoxy-prolyl-dehydrophenylalanyl-histidyl-leucine, and its stereoisomers;
Leucyl-dehydrophenylalanyl-valyl-phenylalanine methyl ester;
3 mercaptopropionyl-prolyl-dehydrophenylalanyl-histidyl-leucine
3 mercapto-2-methylpropionyl-prolyl-dehydrophenylalanyl-histidyl-leucine;
3 mercaptopropionylprolyl-dehydrophenylalanyl-histidine;
3-mercapto-2-methylpropionylprolyl-dehydrophenylalanyl-histidine N-carbobenzoxy-L-prolyl-dehydrophenylalanyl-L-phenylalanine;
N-carbobenzoxy-L-prolyl-dehydrophenylalanine alpha phenethyl amide;
N-carbobenzoxy-DL-prolyl-dehydrophenylalanine alpha phenethyl amide;
N-carbobenzoxy-L-prolyl-dehydrophenylalanyl-L-phenylalanine methyl ester;
N-carbobenzoxy-L-prolyl-dehydrophenylalanine;
L-prolyl-dehydrophenylalanine;
N-carbobenzoxy-phenylalanyl-dehydrophenyl-alanine;
Sarcosyl-arginyl-valyl-dehydrotyrosyl-isoleucyl-histidyl-prolyl-alanine;
Sarcosyl-arginyl-valyl-dehydrotyrosyl-isoleucyl-histidyl-prolyl-threonine methyl ether
Sarcosyl-arginyl-valyl-tyrosyl-isoleucyl-dehydro-histidyl-prolyl-alanine;
Sarcosyl-arginyl-valyl-dehydrotyrosyl-isoleucyl-dehydrohistidyl-prolyl-alanine;
Aspartyl-arginyl-valyl-tyrosyl-isoleucyl-histidyl-prolyl-dehydrophenylalanyl-histidyl-leucine;
Aspartyl-arginyl-valyl-tyrosyl-isoleucyl-histidyl-prolyl-phenylalanyl-dehydrohistidyl-leucine;
Aspartyl-arginyl-valyl-tyrosyl-isoleucyl-histidyl-prolyl-dehydrophenylalanine.

One purpose in introducing unsaturation into a peptide chain is to increase the binding of the peptides to active sites and protect the peptide from enzymatic cleavage, e.g. hydrolysis, in the bloodstream, thus enhancing activity. One method of measuring the stability of peptides to enzymatic hydrolysis is to treat the peptides with chymotrypsin which is specific for phenyl bonds. I have found that N-blocked prolyl-dehydrophenylalanyl-phenylalanine, which is produced by reacting the azlactone of N-blocked prolyl dehydrophenylalanine with the tetramethyl guanidinium salt of phenylalanine in boiling aqueous acetone, is stable to chymotrypsin.

N-benzyloxycarbonyl prolyl-dehydrophenylalanyl-histidinyl-leucine, the analog of the C-terminal tetrapeptide sequence of angiotensin I, was found to inhibit angiotensin I converting enzyme. When the tetrapeptide was freed of the blocking group by HBr/HOAc is was found to be inactive as an enzyme inhibitor.

When glycyl-dehydrophenylalanine is introduced into bradykinin (BDK) at the 4 and 5 positions (BDK is Arg$^1$-Pro$^2$-Pro$^3$-Gly$^4$-Phe$^5$-Ser$^6$-Pro$^7$-Phe$^8$-Arg$^9$) the BDK analog shows surprising activity in the guinea pig ileum contraction assay, i.e., with BDK as the standard at 100% dehydro BDK shows a 247.6% increase in contraction. In addition, in the guinea pig blood pressure test, with BDK as the standard at 100%, the dehydro BDK decreased blood pressure to the extent of 6250% when given intravenously and when given intra-arterially the reduction was 277.7%.

Dehydro BDK can be prepared by solid phase protein synthesis using a mixed anhydride coupling reaction.

In addition, the dehydro phenylalanine analog of the long acting commercial analog of methionine enkaphalin is active in the guinea pig ileum contraction assay. This analog can also be made by solid phase protein synthesis. The compound leudehydrophe-val-phe.OMe which inhibits renin can be produced from the azlactone of N-blocked leucyl-dehydrophenylalanine by reaction with valyl-phenylalanine tetramethyl guanidinium salt to form the N-blocked compound leucyl-dehydrophenylalanyl-valyl-phenylalanine which can be deblocked by treatment with HBr/HOAc, then esterified.

It is also possible to introduce dehydropeptides into peptide hormones such as LH-RH (a decapeptide) as well as the phenylalanine analog of TRH (a tripeptide).

Dehydropolypeptides can be produced either by conventional peptide synthesis once the dehydrodipeptide is made available by the process of this invention or the unsaturated azlactones of this invention can be used as precursors of polypeptides using various routes.

The unsaturated azlactones can be converted directly into a dehydrodipeptide by the reaction with 32% hydrogen bromide in acetic acid at room temperature for about ½ to 1½ hours. The resulting hydrobromide salt of the dehydropeptide can be recovered by precipitation.

In order to use the unsaturated azlactone for other reactions, the N-blocked dehydrodipeptide can be made by hydrolyzing the azlactone with 1 N NaOH, removing the amount of product desired for other uses, then reforming the unsaturated azlactone by cyclizing the N-blocked dehydrodipeptide with dicyclohexyl carbodiimide.

The N-blocked dehydropeptide can be freed of the blocking group by treatment with hydrogen bromide in acetic acid.

The N-blocked unsaturated azlactone can be converted by any one of three reaction sequences into a dehydropolypeptide.

The most direct sequence is to treat the azlactone with the tetramethyl guanidinium salt of the peptide sequence to be added then deblocking the product with hydrogen bromide in acetic acid. The following reaction scheme illustrates this reaction.

REACTION SCHEME II

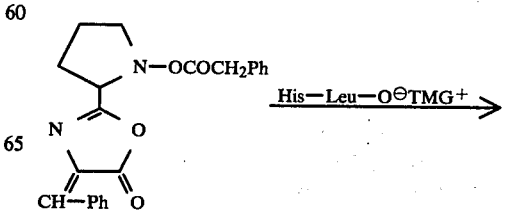

-continued
REACTION SCHEME II

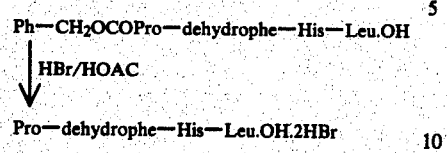

A second reaction sequence is to treat the N-blocked unsaturated azlactone with the ester of the desired peptide sequence to be added in hot aqueous acetone, treating the resulting product with a base to remove the ester group then deblocking the terminal amino nitrogen by treatment with hydrogen bromide in acetic acid. The following illustrates the reaction sequence.

REACTION SCHEME III

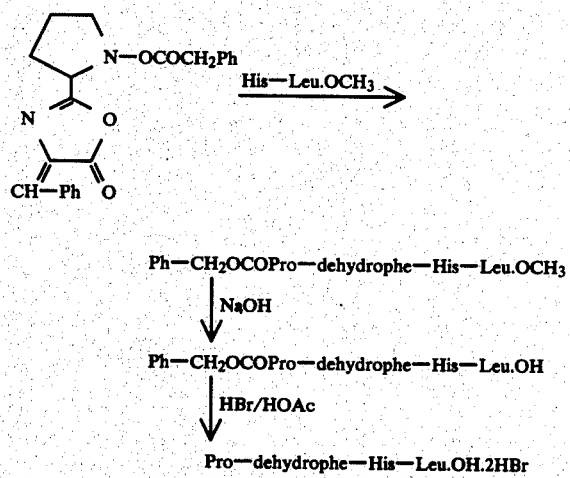

A third reaction sequence is to hydrolyze the N-blocked unsaturated dehydro azlactone with 1 N NaOH then treat the resulting product by the mixed anhydride method to produce the ester as in Reaction Scheme III, then following Reaction Scheme III to the final product. This reaction can be illustrated by the following sequence.

REACTION SCHEME IV

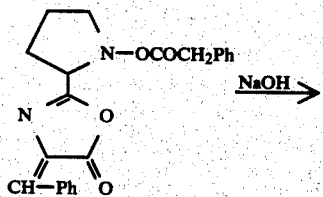

REACTION SCHEME IV (continued)

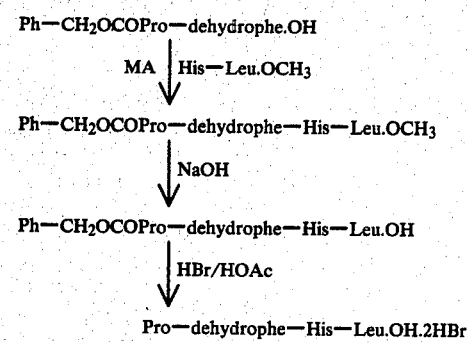

A fourth reaction sequence is to prepare an intermediate for use in the known solid phase peptide synthesis reaction. See Stewart et al., "Solid Phase Peptide Synthesis," Freeman Press, San Francisco (1969). The intermediate is prepared by reacting a dehydro azlactone of Formula II with a polymer conjugated peptide of the desired sequence at 20°–80° C. in a solvent such as ethyl acetate or dimethyl formamide according to the following reaction sequence.

REACTION SCHEME V

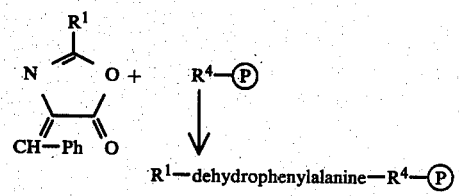

wherein $R^1$ has the same meaning as in Formulas I and II; $R^4$ is an amino acid or peptide chain and (P) is a solid polymer such as a polydimethyl acrylamide or polystyrene.

The N-blocking group of the intermediate is removed by treatment with a conventional deblocking reagent. The addition of N-blocked amino acids is then made in the desired sequence by first adding an N-blocked amino acid to the peptide then deblocking and adding amino acids in the sequence desired. The polymer is removed by conventional means, e.g., treatment with HF or trifluoroacetic acid.

Dehydropeptides which can be made in this manner are, for example:
Arginyl-prolyl-prolyl-glycyl-dehydrophenylalanyl-seryl-prolyl-phenylalanyl-arginine;
Sarcosyl-arginyl-valyl-dehydrotyrosyl-isoleucyl-histidyl-prolyl-alanine;
Sarcosyl-arginyl-valyl-tyrosyl-isoleucyl-dehydrohistidyl-prolyl-alanine;
Sarcosyl-arginyl-valyl-dehydrotyrosyl-isoleucyl-dehydrohistidyl-prolyl-alanine;
Aspartyl-arginyl-valyl-tyrosyl-isoleucyl-histidyl-prolyl-dehydrophenylalanyl-histidyl-leucine;
Aspartyl-arginyl-valyl-tyrosyl-isoleucyl-histidyl-prolyl-phenylalanyl-dehydrohistidyl-leucine;
Aspartyl-arginyl-valyl-tyrosyl-isoleucyl-histidyl-prolyl-dehydrophenylalanine.

The dehydropeptide of this invention can be used in the same manner for the same activity as a peptide analog with the same dosage form; e.g., oral or parenteral.

The dosages are adjusted to the needs of the individual patient as determined by the clinician and generally are lower than the dosages of the saturated peptide. The oral dosage forms; e.g. tablets, suspensions, solutions, capsules and the like can be prepared using conventional inert adjuvant materials. Parenteral dosage forms can be prepared using conventional parenteral adjuvant materials.

The following examples illustrate the invention. All melting points were determined on an electrothermal melting point apparatus and are uncorrected. Infrared spectra were taken on a Perkin-Elmer Model 257 or 237-B recording spectrometer with polystyrene as the standard. The $^1$HNMR spectra were taken on a Perkin-Elmer T-60 spectrometer with tetramethylsilane as the internal standard. Optical rotations were obtained on an O. C. Rudolph and Sons Model 80 polarimeter. Elemental analyses were carried out by Atlantic Microlabs, Atlanta, Ga. Thin layer chromatography was carried out on Kodak ultraviolet-sensitive silica gel sheets, which were visualized by uv, ninhydrin (N) and Pauly (P) color tests. The solvent systems were A: N-butyl alcohol-acetic acid-water, 7:1:2; B: 2-propanol-water, 5:1; C: n-butyl alcohol-acetone-acetic acid-5.6% ammonia, 9:3:2:4. All temperatures are in degrees Celsius.

EXAMPLE 1

(a) Azlactone of N-Carbobenzoxy-L-prolyl-L-phenylalanine

There was added 1.2 g (0.006 mole) of dicyclohexyl carbodiimide to a solution of 2 g (0.005 mole) of N-carbobenzoxy-L-prolyl-L-phenylalanine in 15 ml of dry tetrahydrofuran. The mixture was allowed to stand in the refrigerator overnight; the resulting precipitated urea was filtered and the filtrate was evaporated to dryness. The residual oil which resulted was crystallized from ether/petroleum ether yielding 1.7 g (89%) of azlactone of N-carbobenzoxy-L-prolyl-L-phenylalanine, mp 92°–94°. A second recrystallization from ether/petroleum ether gave an analytical sample, mp 101°–102°, $[\alpha]_D^{26} = -72.5°$ (c, 2% in THF); ir(CHCl$_3$) 1830 (C=O), 1720–1700 (C=O), 1610 am$^{-1}$ (C=N); NMR (CDCl$_3$)σ:1.17–2.17 (m, 4H, Pro ring), 2.8–3.33 (m, 2H, >CH—C$\underline{H}_2$Ph), 3.33–3.70 (m, 2H, Pro ring, 4.0–4.43 (m, 1H, =N—C$\underline{H}$—CH$_2$Ph), 4.33–4.73 (m, 1H, Pro ring), 5.17 (br.s., 2H, >N—OCO C$\underline{H}_2$Ph), 7.25 (s, 5H, Ar$\underline{H}$), 7.35 ppm (s, 5H, Ar$\underline{H}$).

Anal. Calcd. for C$_{22}$H$_{22}$N$_2$O$_4$; C, 69.83; H, 5.86; N, 7.40. Found: C, 69.74; H, 5.87; N, 7.36.

(b) Azlactone of N-Carbobenzoxy-L-prolyl-dehydrophenylalanine.

0.454 g (0.002 mole) of DDQ were added to a solution of 0.756 g (0.002 mole) of azlactone of N-carbobenzoxy-L-prolyl-L-Phenylalanine in 20 ml of dry 1,2-dimethoxyethane; then 0.244 g (0.002 mole) of collidine were added. The resulting reaction mixture was stirred at room temperature (20°–25°) for 6 days, the precipitate was filtered and the filtrate was evaporated in vacuo. The resulting residual oil was dissolved in ethyl acetate and the solution was washed with N-hydrocholoric acid, saturated sodium bicarbonate, saturated sodium chloride solution and dried over anhydrous Na$_2$SO$_4$. The solvent was evaporated in vacuo and the residual oil was purified on a column of silica gel (60–200 mesh) by elution with ether/petroleum ether (1:1) yielding a yellow oil which was crystallized from ether/petroleum ether to give 0.364 g (48%) of azlactone of N-carbobenzoxy-L-prolyl-L-dehydrophenylalanine, mp 90°–92°. Re-crystallization from ether/petroleum ether resulted in an analytical sample, mp 93°–94.5°, Rf 0.39 (ether/petroleum ether, 1:1), $[\alpha]_D^{29} = -69°$ (c, 1% in THF), ir (CHCl$_3$) 1800 (C=O), 1725–1710 (C=O), 1645 cm$^{-1}$ (C=N), NMR (CDCl$_3$) δ:1.83–2.67 (m,4H, Pro ring), 3.5–4.0 (m,1H, Pro ring), 5.23 (s, 2H, >N—OCOC$\underline{H}_2$Ph), 7.0–7.7 (m, 9H, Ar$\underline{H}$ and PhC$\underline{H}$=C), 7.9–8.3 ppm (m, 2H, Ar$\underline{H}$).

Anal. Calcd. for C$_{22}$H$_{20}$N$_2$O$_4$: C, 70.20; H, 5.36; N, 7.44. Found: C, 70.26; H, 5.44; N, 7.52.

EXAMPLE 2

Azlactone of N-Carbobenzoxy-L-prolyl-dehydrophenylalanine

To a solution of 2.2 g (0.0072 mole) of Ncarbobenzoxy-L-prolyl-glycine in 25 ml of dry tetrahydrofuran, there was added 1.8 g (0.009 mole) of dicyclohexylcarbodiimide. The resulting mixture was allowed to stand in a refrigerator overnight; the precipitated urea which precipitated was filtered and the filtrate was concentrated to dryness in vacuo. The resulting residual oil was dissolved in 3.5 ml of acetic anhydride and 0.72 g (0.0072 mole) of benzaldehyde then 0.709 g (0.0086 mole) of anhydrous sodium acetate were added. After five days at room temperature the reaction mixture was neutralized with saturated sodium bicarbonate solution and the separated oil was extracted into ethyl acetate. The extracts were washed with saturated sodium bisulfite solution, saturated sodium bicarbonate solution, saturated sodium chloride solution and dried over anhydrous Na$_2$SO$_4$. The solvent was evaporated in vacuo and the residual oil was purified on a column of silica gel (60–200 mesh) by elution with ether/petroleum ether (1:1) yielding an oil. Crystallization from ether/petroleum ether gave 0.416 g (15%) of azlactone of N-carbobenzoxy-L-prolyl-dehydrophenylalanine, mp 89°–91°, $[\alpha]_D^{30} = -69.1°$ (C, 1% in THF)

EXAMPLE 3

N-Carbobenzoxy-L-prolyl-dehydrophenylalanine

There was added 3 ml of N-sodium hydroxide to a solution of 0.753 g (0.002 mole) of the azlactone of N-carbobenzoxy-L-prolyl-dehydrophenylalanine in 7 ml of Acetone. The resulting mixture was stirred at room temperature for 30 min., then concentrated in vacuo. The residual aqueous solution was washed with ethyl acetate and acidified with 4 N-hydrochloric acid. The resulting separated oil was extracted with ethyl acetate and the combined extracts were dried over anhydrous Na$_2$SO$_4$. The solvent was evaporated in vacuo and the residual oil was chromatographed on a silica gel (60–200 mesh) column by elution with ether. The resulting oily product was dried in vacuo over phosphorous pent oxide giving 0.5 g (63%) of amorphous solid, R$_f$0.68, $[\alpha]_D^{28} = +41.6°$ (c, 1% in THF); ir (CHCl$_3$) 2895 (COOH), 1700 (C=O), 1685 (C=O), 1650 cm$^{-1}$ (C=C); NMR (CDCl$_3$) δ1.5–2.4 (m, 4H, Pro ring), 3.23–3.77 (m, 2H, Pro ring), 4.4–4.67 (m, 1H, Pro ring), 5.17 (s, 2H, >N—OCOC$\underline{H}_2$Ph), 6.5–6.83 (br.s, 1H, —N$\underline{H}$, exchanged by D$_2$O), 7.37 (br., s, 9H, Ar$\underline{H}$, and PhC$\underline{H}$=C—), 7.5 (br.s. 2H, Ar$\underline{H}$), 7.83–8.4 ppm (b, 1H, —N$\underline{H}$, exchanged by D$_2$O).

Anal. Calcd. for C$_{22}$H$_{22}$N$_2$O$_5$ ⅓ H$_2$O: C, 66.00; H, 5.67; N, 7.00. Found: C, 66.01; H, 5.69; N, 6.98.

EXAMPLE 4

N-Carbobenzoxy-L-prolyl-dehydrophenylalanyl-L-phenylalanine methyl ester

A mixture of 0.759 g (0.0036 mole) of L-phenylalanine methyl ester hydrochloride and 40 ml of ethyl acetate was cooled in an ice-bath and 15 ml of cold 50% potassium carbonate solution was added. The mixture was equilibrated, and the ethyl acetate layer was separated and dried over anhydrous Na$_2$SO$_4$ at 0°. To the solution 1.129 g (0.003 mole) of the azlactone of N-carbobenzoxy-L-prolyl-dehydrophenylalanine was added. The reaction mixture was then refluxed for 8 hours, cooled and washed with N-hydrochloric acid, saturated sodium bicarbonate solution, saturated sodium chloride solution and dried over anhydrous Na$_2$SO$_4$. The solvent was evaporated in vacuo and the residual crystals were recrystallized from ethyl acetate/petroleum ether giving 1.473 g (88%) of N-carbobenzoxy-L-prolyl-dehydrophenylalanyl-L-phenylalanine methyl ester, mp 161°–163.5°, R$_f$0.95, $[\alpha]_D^{26} = -94.3°$ (c, 1% in EtOH); ir (CHCl$_3$) 1735 (C=O) 1690–1670 (C=O), 1630 cm$^{-1}$ (C=C); NMR (CDCl$_3$) δ1.5–2.4 (m, 4H, Pro ring), 3.0–3.33 (m, 2H, —CHCH$_2$Ph), 3.33–3.57 (m, 2H Pro ring) 3.63 (s, 3H, —COOCH$_3$), 4.17–4.53 (m, 1H, —CH—CH$_2$Ph), 4.67–5.0 (m, 1H, Pro ring), 5.02 (br.s., 2H>NOCOCH$_2$Ph) 6.83–7.47 (m, 11H, ArH and PhCH=C<), 7.9–8.1 ppm (b, 2H, NH, exchang by D$_2$O).

Anal. Calcd. for C$_{32}$H$_{33}$N$_3$O$_6$: C, 69.17; H, 5.99; N, 7.56. Found: C, 69.16; H, 6.02; N, 7.56.

EXAMPLE 5

N-Carbobenzoxy-L-prolyl-dehydrophenylalanyl-L-phenylalanine (a) There was added 2 ml of N-sodium hydroxide to a solution of 0.556 g (0.001 mole) of N-carbobenzoxy-L-prolyl-dehydrophenylalanyl-L-phenylalanine methyl ester in 10 ml of methanol. The mixture was stirred at room temperature for 2 hours and concentrated in vacuo. The residual aqueous solution was washed with ethyl acetate and after acidification with 4 N-hydrochloric acid, the resulting separated oil was extracted into ethyl acetate and the extracts were dried over anhydrous Na$_2$SO$_4$. The solvent was evaporated in vacuo and the residual oil was purified on a column of silica gel (60–200 mesh) by elution with ether. The oily product was crystallized from ether to yield 0.357 g (66%) of N-carbobenzoxy-L-prolyl-dehydrophenylalanyl-L-phenylalanine, mp 171°–173°, R$_f$0.68, $[\alpha]_D^{26} = -30.2°$ (c, 1% in THF); ir (CHCl$_3$) 1730 (Sh, C=O), 1670 (C=O), 1630 cm$^{-1}$(Sh,C=C); NMR (CDCl$_3$) δ1.5–2.3 (m, 4H, Pro ring), 3.0–3.5 (m, 2H, >CH—CH$_2$Ph), 3.2–3.7 (m, 2H, Pro ring), 4.2–4.5 (m, 1H>CHCH$_2$Ph), 4.6–5.0 (m, 1H, Pro ring), 5.0 (s, 2H, >N—O-COCH$_2$Ph), 7.0–7.6 (m, 16H, ArH and PhCH=C—), 8.0–8.27 (br, 1H, —NH exchanged by D$_2$O); 9.03–9.5 (br, 2H, —NH or —COOH, exchanged by D$_2$O.

Anal. Calcd. for C$_{31}$H$_{31}$N$_3$O$_6$: C, 68.75; H, 5.77; N, 7.76. Found: C, 68.67; H, 5.79; N, 7.76.

(b) There was added 0.752 g (0.002 mole) of N-carbobenzoxy-L-prolyl-dehydrophenylalanine Azlactone to a solution of 0.397 g (0.0024 mole) of L-phenylalanine and 0.276 g (0.0024 mole) of 1,1,3,3-tetramethylguanidine in 10 ml of acetone:water (4:1). The resulting solution was refluxed 15 hours and concentrated in vacuo. The residual aqueous solution was acidified with 4 N-hydrochloric acid and the precipitate was extracted into ethyl acetate. The extracts were washed with N-hydrochloric acid and saturated sodium chloride solution, then dried over anhydrous Na$_2$SO$_4$. The solvent was evaporated in vacuo and the residual oil was purified on a column (2.0×18 cm) of silica gel by elution with ether. Crystallization of the oily product from ether/petroleum ether yielded 0.760 g (70%) of N-carbobenzoxy-L-prolyl-dehydrophenylalanyl-L-phenylalanine, mp 171°–173°, R$_f$0.67, $[\alpha]_D^{25} = -29.9°$ (c, 1% in THF).

EXAMPLE 6

L-Prolyl-dehydrophenylalanine Hydrobromide (a) A solution of 0.564 g (0.0015 mole) of N-carbobenzoxy-L-prolyl-dehydrophenylalanine Azlactone was dissolved in 3 ml of 32% HBr/HOAc and was stirred at room temperature for 30 minutes. The resulting mixture was added dropwise to anhydrous ether; the precipitate which formed was filtered and recrystallized from methanol/petroleum ether giving 0.449 g (88%) of L-prolyl-dehydrophenylalanine Hydrobromide, mp 227°–228° (dec.), R$_f$0.46, $[\alpha]_D^{30} = +52.7°$ (c, 1% in CH$_3$OH); ir (CHCl$_3$); 1700 (C=O), 1682 (C=O), 1635 cm$^{-1}$ (C=C); NMR (DMSO-D$_6$) δ1.67–2.33 (m, 4H, Pro ring), 3.0–3.7 (m, 2H Pro ring 4.5 (m, 1H, Pro ring), 7.1–7.95 (m, 6H, ArH and PhCH=C—), 8.17–8.83 (br., 1H, NH, exchanged by D$_2$O), 9.0–9.67 (br., 1H, NH, exchanged by D$_2$O), 10.0 (s, 1H, —COOH, exchanged by D$_2$O).

Anal. Calcd. for C$_{14}$H$_{16}$N$_2$O$_3$HBr: C, 49.24; H, 5,03; N, 8.21. Found: C,49.28; H, 4.99; N, 8.21.

(b) A solution of 0.5 g (0.00125 mole) of N-carbobenzoxy-L-prolyl-dehydrophenylalanine in 3 ml of 32% HBr/HOAc was treated as N-carbobenzoxy-L-prolyl-dehydrohpenylalanine azlactone was treated in Example 7(a) except that the ether precipitated product was allowed to stand two days at room temperature before filtration and crystallization from methanol/ethyl acetate to yield 0.313 g (74%) of L-prolyldehydrophenylalanine hydrobromide, m.p. 227°–228.5° (dec.), R$_f$0.45.

EXAMPLE 7

N-Carbobenzoxyglycyl-DL-phenylalanine (a) A solution of 4.2 g (0.02 mole) of N-carbobenzoxyglycine and 2.2 g (0.022 mole) of N-methylmorpholine in 50 ml of dry toluene was cooled to −5° and 2.8 g (0.02 mole) of isobutyl chloroformate was added thereto. After 1 hour, a solution of 3.3 g (0.02 mole) of DL-phenylalanine in 20 ml of N-sodium hydroxide was added and the mixture was stirred vigorously overnight. The aqueous phase was isolated, extracted with ether and acidified with 4 N Hydrochloric acid to precipitate the product as a colorless oil which crystallized upon cooling. Recrystallization from ethanol-water yielded 5 g (70%) of N-carbobenzoxyglycyl-DL-phenylalanine, mp 158°–160° C., R$_f$0.61.

Azlactone of N-Carbobenzoxyglycyl-DL-phenylalanine (b) There was added 2.2 g (0.011 mole) of dicyclohexylcarbodiimide to a mixture of 3.5 g (0.01 mole) of N-carbobenzoxyglycy-DL-phenylalanine in 20 ml of dry tetrahydrofuran at room temperature. The resulting mixture was allowed to stand in a refrigerator overnight, the dicyclohexylurea which formed was filtered off and the solvent was evaporated in vacuo. The resulting residual oil was dissolved in ether, a small amount of hexane was added and the solution was allowed to stand in a refrigerator yielding 2.6 (78%) of azlactone of N-carbobenzoxyglycyl-DL-phenylalanine, mp 71°–72.5° C., ir (CHCl$_3$) 3360 (NH), 1830 (azlactone C=O) 1725 (Z, C=O), 1675 cm$^{-1}$ (C=N); NMR (CDCl$_3$) δ2.87–3.20 (m, 2H, PhC$\underline{H}_2$CH), 3.80–4.10 (m, 2H, —C$\underline{H}_2$—NH—), 4.17–4.50 (m, 1H, PhCH$_2$C$\underline{H}$), 5.1 (s, 2H, PhC$\underline{H}_2$OCONH—), 5.62 (br, 1H, —N$\underline{H}$), 7.22 (s, 5H, Ph), 7.35 ppm (s, 5H, Ph).

Azlactone of N-Carbobenzoxyglyclydehydrophenylalanine (c) A solution of 0.674 g (2 Mmole) of azlactone of N-carbobenzoxyglycyl-DL-phenylalanine in 20–30 ml of dry dimethoxyethane containing equimolar amounts of DDQ and base, e.g. pyridine, imidazole or collidine, was stirred at ambient temperature until the reaction was completed. The solvent was evaporated in vacuo, and the residual brown syrup was purified by percolation through a 20 cm×2 cm column of silica gel (60–200 mesh) by using ether/petroleum ether (1:1) as eluant. Recrystallization from ethyl acetate-petroleum ether yielded zlactone of N-arbobenzoxyglyclydehydrophenylalanine, mp 138°–140°, ir (CHCl$_3$) 3360 (NH), 1810 azlactone (C=O), 1775 (C=O), 1725 (Z, C=O), 1660 cm$^{-1}$ (C=N); NMR (CDCl$_3$) δ4.33 (d, 2H, C$\underline{H}_2$NHZ), 5.13 (s, 2H, NHOCOC$\underline{H}_2$Ph) 5.33–5.70 (b, 1H, NHZ), 7.10–7.57 (m, 9H, ArH and PhC$\underline{H}$=), 7.83–8.23 (m, 2H, ArH).

EXAMPLE 8

N-Carbobenzoxyglyclydehydrophenylalanine

A solution of 1.00 g (0.003 mole) of azlactone of N-carbobenzoxyglyclydehydrophenylalanine in 30 ml of acetone-water (2:1) was refluxed 12 hours. The solution was evaporated in vacuo and the resulting crystalline residue was recrystallized from ethyl acetate-petroleum ether yielding 0.95 g (89%) of N-carbobenzoxyglyclydehydrophenylalanine, mp 173°–174.5° R$_f$0.78; ir (Nujol) 3350, 3250 (NH), 1700 (c=O), 1670 cm$^{-1}$ (C=O); NMR (CF$_3$COOH), δ4.33 (s, 2H, —NHCH$_2$CO—), 5.31 (s, 2H, HNOCOC$\underline{H}_2$Ph), 7.40–7.70 ppm (m, 11H, ArH and PhC$\underline{H}$=).

EXAMPLE 9

Glyclydehydrophenylalanine Hydrobromide (a) There was added 3 ml of 32% hydrogen bromide in acetic acid to 0.531 g (0.0015 mole) of N-carbobenzoxyglyclydehydrophenylalanine and the resulting mixture was stirred at room temperature. Upon cessation of carbon dioxide evolution (about 20 minutes), anhydrous ether was added and the precipitate which formed was filtered and washed with several portions of anhydrous ether. Recrystallization from methanol-ethyl acetate yielded 0.38 g (80%) of Glyclydehydrophenylalanine Hydrobromide, mp 224°–225° (decomp.), R$_f$0.55; ir (Nujol) 1690 (C=O), 1670 (C=O), 1640 cm$^{-1}$ (C=C); NMR (Me$_2$SO-d$_6$) δ3.8 (s,2H, —C$\underline{H}_2$CONH—), 5.0–6.6 (br, 3H, N$\underline{H}_3$—CH$_2$CO, exchanged in D$_2$O), 7.3–7.8 (6H, m, Ar$\underline{H}$ and PhC$\underline{H}$=), 7.9–8.5 (br, 2H, —N$\underline{H}$ and —COO$\underline{H}$, exchanged in D$_2$O).

Anal. Calcd. for C$_{11}$H$_{12}$O$_3$N$_2$.HBr.H$_2$O: C, 41.39; H, 4.70; N, 8.78. Found: C, 41.36; H, 4.75; N, 8.78.

(b) 0.531 g (0.0015 mole) of N-carbobenzoxyglyclydehydrophenylalanine was dissolved in 20 ml of methanol and 0.3 g of 5% Pd/C and 1.5 ml (0.0015 mole) of N-hydrogen bromide in acetic acid were added. A stream of hydrogen gas was passed through the stirred solution. Upon cessation of carbon dioxide evolution (about 15 minutes), the catalyst was removed by filtration, washed with a little methanol, and the combined filtrate and washing were concentrated in vacuo. The residual oil was crystallized from anhydrous ether yielding 0.186 g (39%) of Glyclydehydrophenylalanine Hydrobromide, mp 222°–224°, R$_f$0.55. Another product in the mother liquor had R$_f$0.32, equal to that of glycyl-DL-phenylalanine hydrobromide.

(c) There was added 3 ml of 32% hydrogen bromide in acetic acid to 0.5037 g (0.0015 mole) of the azlactone of N-carbobenzoxyglyclydehydrophenylalanine and the resulting mixture was stirred at room temperature. The product which formed was worked up using the procedure described in Example 11(a) and has an mp 219°–221° (dec.) (76% yield), R$_f$0.55, and was identical in all respects to that obtained in Example 9(a).

(d) 0.2 g (0.002 mole) of acetic anhydride was added to 3 ml of 32% hydrogen bromide in acetic acid, and the resulting mixture was allowed to stand at room temperature for 30 minutes. Thereto, 0.336 g (0.001 mole) of the azlactone of N-carbobenzoxyglycyldehydrophenylalanine was added and the resulting solution was stirred at room temperature. After 30 minutes, glyclydehydrophenylalanine hydrobromide precipitated. It was filtered and washed with anhydrous ether. Recrystallization from methanol-ethyl acetate yielded 0.290 g (91%) of glyclydehydrophenylalanine hydrobromide, mp 221°–223° (decomp.). The product was identical to that obtained from Example 9(c).

EXAMPLE 10

Z-Pro-ΔPhe-His-Leu.OCH$_3$*

(a) A solution of 1.2 g (0.003 mole) of Z-Pro-ΔPhe.OH in 20 ml of dry tetrahydrofuran (THF), was cooled to −5° and 0.36 g (0.0036 mole) of N-methylmorpholine and 0.42 g (0.003 mole) of isobutyl chloroformate were added. After 1 hour a solution of 1.3 g (0.003 mole) of H.His-Leu.OME.2HBr, prepared from Z-His-Leu.OCH$_3$ with HBr/HOAc, in 10 ml of dioxane:water (7:3) containing 0.72 g (0.0072 mole) of triethylamine was added. The resulting mixture was stirred at room temperature for 3 hours, water was added and the THF was removed in vacuo. The separated oil was extracted into chloroform and the combined extracts were washed with saturated sodium chloride solution and dried over anhydrous Na$_2$SO$_4$. The solvent was evaporated in vacuo and the residual solid was purified on a column of silica gel (60–200 mesh) by elution with chloroform: Methanol (5:1) yielding 1.65 g (84%) of amorphous Z-Pro-ΔPhe-His-Leu.OCH$_3$, R$_f$0.83, R$_f^B$0.92, R$_f^C$0.89 [α]$_D^{22}$= −27.3° (c, 2.3% in CH$_3$OH); P(+), N(−).

*Z is N-carbobenzoxy; ΔPhe is dehydrophenylalanine.

(b) H.His-Leu.OMe.2HBr (0.9 g, 0.002 mole) was dissolved in 20 ml of 4:1 mixture of water and acetone and 0.4 g (0.004 mole) of triethylamine was added. To the resulting solution there was added 0.752 g (0.002 mole) of the azlactone of Z-ProΔPhe-OH. The resulting mixture refluxed for 24 hours, water was added and the acetone was removed in vacuo. The separated oil was extracted into chloroform and the combined extracts were washed with saturated sodium chloride and dried over anhydrous Na$_2$SO$_4$. The solvent was evaporated in vacuo and the residual solid was purified on a column of silica gel (60–200 mesh) by elution with chloroform:methanol (5:1) yielding 1 g (76%) of amorphous Z-Pro-ΔPhe-His-Leu.OCH$_3$ R$_f$0.83, R$_f$0.92, R$_f$0.89 [α]$_D^{22}$=−27.4° (c, 2.3% in CH$_3$OH).

EXAMPLE 11

Z-Pro-ΔPhe-His-Leu.OH (a) Z-Pro-ΔPhe-His-Leu.OCH$_3$ (1.65 g) was dissolved in a solution of N-sodium hydroxide (3 ml) and acetone (10 ml), which was stirred at room temperature for 2 hours. Water was added and the acetone was removed in vacuo. The residual aqueous solution was acidified with saturated citric acid to pH 3. The resulting separated oil was extracted into chloroform and the combined extracts were washed with water and dried over anhydrous Na$_2$SO$_4$. The solvent was evaporated in vacuo and the residual syrup was crystallized from chloroform ether yielding 1.04 g (64%) of amorphous Z-Pro-ΔPhe-His-Leu.OH, mp 150°–155°, R$_f$0.68, R$_f$0.64, R$_f$0.72, [α]$_D^{22}$=+4.8° (C, 1.6% in N-NaOH), P(+) Pro:His:Leu::1.03:0.97:1.01.

(b) H.His-Leu.OH (0.508 g, 0.002 mole) and 0.23 g (0.002 mole) of 1,1,3,3,-tetramethylguanidine were dissolved in a 24 ml of a 1:5 mixture of water and acetone. 0.752 g (0.002 mole) of Z-Pro-ΔPhe azlactone was added to the solution. The resulting mixture was refluxed 24 hours, water was added and the acetone was removed in vacuo. The residual aqueous solution was acidified with saturated citric acid to pH 3 and the separated oil was extracted into chloroform. The combined extracts were washed with water and dried over anhydrous Na$_2$SO$_4$. The solvent was evaporated in vacuo and the residual syrup was crystallized from chloroform-ether yielding 1.04 g (81%) of amprphous Z-Pro-ΔPhe-His-Leu.OH, mp 149°–154°, R$_f$0.67, R$_f$0.64, R$_f$0.72; [α]$_D^{32}$=+5.1° (C, 2.1% in N—NaOH).

EXAMPLE 12

H.Pro-ΔPhe-His-Leu.OH.2HBr

Z-Pro-ΔPhe-His-Leu.OH (0.322, 0.5 mole) was dissolved in 2 ml of 32% hydrogen bromide in acetic acid and the mixture was stirred at room temperature for 30 min. The reaction mixture was poured into 100 ml of anhydrous ether and the precipitate which formed was collected by filtration, dissolved in methanol and the methanol was evaporated in vacuo to remove excess HBr. The residual solid was recrystallized from 2-propanol/ether yielding 0.233 g (69%) of crystalline H.Pro-ΔPhe-His-Leu.OH.2HBr. Purification on a column of Bio-Gel P-2 (100–200 mesh) gave an analytical sample, mp 162°–168° (dec.), R$_f$0.64, R$_f$0.76, R$_f$0.65; P,N(+); Pro:His:Leu::1.02:1.00:0.98.

Anal. Calcd. for C$_{26}$H$_{34}$N$_6$O$_5$.2HBr.H$_2$O: C, 45.23; H, 5.22; N, 12.18. Found: C, 45.15; H, 5.29; N, 11.77.

EXAMPLE 13

Racemization of N-Carbobenzoxy-L-prolyl-dehydrophenylalanine Azlactone 0.2 g (0.002 mole) of triethylamine was added to a solution of 0.753 g (0.002 mole) of N-carbobenzoxy-L-prolyl-dehydrophenylalanine azlactone in 15 ml of dry tetra hydrofuran. The solvent was evaporate in vacuo; the residual oil was dissolved in ethyl acetate and the solution was washed with N HCl, saturated sodium bicarbonate solution and water. After drying over anhydrous Na$_2$SO$_4$ the solvent was evaporated in vacuo and the residual oil was purified on a column of silica gel (60–200 mesh) by elution with ether/petroleum ether (1:1). Crystallization of the oil from ether/petroleum ether yielded 0.460 g (61%) or racemic N-carbobenzoxy-L-prolyl-dehydrophenylalanine azlactone, mp 87°–89°; [α]$_D^{27}$=0° (c, 1% in THF); R$_f$0.38 (Et$_2$O:pet.ether 1:1); ir (CHCl$_3$) 1800–1780 (C=O), 1720 (Sh), 1700–1680 (C=O), 1655 cm$^{-1}$ (C=N): NMR (CDCl$_3$) δ1.8–2.6 (m, 4H, Pro ring), 3.4–3.9 (m, 2H, Pro ring), 4.7–5.1 (m, 1H, Pro ring), 5.23 (s, 2H, >N-OCOC$\underline{H}_2$Ph) 7.0–7.7 (m, 9H, Ar$\underline{H}$ and PhC$\underline{H}$=C), 7.9–8.3 (m, 2H, Ar$\underline{H}$).

Anal. Calcd. for C$_{22}$H$_{20}$N$_2$O$_4$: C, 70.20; H, 5.36; N, 7.44; Found: C, 70.21; H, 5.37; N, 7.45.

EXAMPLE 14

N-Carbobenzoxy-L-prolyl-dehydrophenylalanineα-phenethyl amide

There was added 0.145 g (0.0012 mole) of (−)-α-phenethylamine [α]$_D^{25}$=−41.1° (c, 1.4% benzene) to a solution of 0.3765 g (0.001 mole) of optically pure N-carbobenzoxy-L- prolyl-dehydrophenylalanine azlactone in 20 ml of dry ethyl acetate. The mixture was refluxed for 15 hours and cooled in an ice-bath. The precipitate which formed was filtered yielding 0.465 g of N-Carbobenzoxy-L-prolyl-dehydrophenylalanineα-phenethyl amide. Recrystallization from ethyl acetate yield a 430 mg (86%) of N-Carbobenzoxy-L-prolyl-dehydrophenylalanineα-phenethyl amide, mp 175°–176°; R$_f$0.94, [α]$_D^{27}$=−105.7° (c, 1% in THF); ir (CHCl$_3$) 3320 (NH), 1700 (Sh, C=O), 1690–1660 (C=O), 1625 cm$^{-1}$ (C=C), NMR (CDCl$_3$) δ:1.5 (d, J=7 cps, 3H, >CHC$\underline{H}_3$), 1.67–2.37 (m, 4H, Pro ring), 3.33–3.77 (m, 2H, Pro ring). 4.17–4.47 (m, 1H, Pro ring), 5.13 (s, 2H, —N—OCOC$\underline{H}_2$Ph), 5.1–5.3 (m, 1H, >C$\underline{H}$—CH$_3$), 7.1–7.7 (m, 16H, Ar$\underline{H}$ and PhC$\underline{H}$=C), 7.9 ppm (br, 2H, —N$\underline{H}$, exchanged by D$_2$O).

Anal. Calcd. for C$_{30}$H$_{31}$N$_3$O$_4$: C, 72.41; H, 6.32; N, 8.49. Found: C, 72.66; H, 6.32; N, 8.49.

EXAMPLE 15

N-Carbobenzoxy-DL-prolyl-dehydrophenylalanine-α-phenethyl amide

Using 0.376 g of racemic N-Carbobenzoxy-prolyl-dehydrophenylalanine azlactone and 0.147 g (0.0012 mole) of (−)-α-phenethylamine, a quantitative yield of amorphous N-Carbobenzoxy-DL-prolyl-dehydrophenylalanine-α-phenethyl amide was obtained by the same procedure as in Example 16. The properties of the product were [α]$_D^{25}$=0° (c, 1% in THF); R$_f$0.94; ir (CHCl$_3$): 3320 (NH), 1700 (Sh C=O), 1690–1660 (C=O), 1625 cm$^{-1}$ (C=C); NMR (CDCl$_3$) δ:1.49 (d, 1.5H, J=7 Hz, (CH$_3$)$_2$C$\underline{H}$—), 1.56 (d, 1.5H, J=7 Hz, (C$\underline{H}_3$)$_2$CH—), 1.87–2.43 (m, 4H, Pro ring), 3.33–3.83 (m, 2H, Pro ring), 4.17–4.57 (m, 1H, Pro ring), 5.15 (s, 2H, >N-OCOC$\underline{H}_2$Ph), 4.83–5.1 and 5.2–5.47 (m, 1H, C$\underline{H}$—CH$_3$), 7.2–7.77 (m, 16H, Ar$\underline{H}$ and PhC$\underline{H}$=C), 7.8–8.03 (b, 2H, N$\underline{H}$). Crystallization of the crude mixture from ethyl acetate/pet.ether yielded a crystalline solid, m.p. 172°–174°, [α]$_D^{25}$ (C, 1% in THF), identical to L,L-diastereomer).

EXAMPLE 16

Enzymolysis of N-Carbobenzoxy-L-prolyl-dehydrophenylalanyl-L-phenylalanine

A solution of 46 mg of N-Carbobenzoxy-L-prolyl-dehydrophenylalanyl-L-phenylalanine in 4 ml of methanol/water (1:1) was diluted to 10 ml with a 0.05 N tris buffer solution (pH 8) containing 0.46 mg of α-chymotrypsin. After standing 2 hours at 37° in a constant temperature bath, a 0.5 ml sample was treated with 0.5 ml of a 1.25% acetone solution of ninhydrin. The color formed matched that of a blank solution while that formed when the saturated tripeptide ZPro-Phe-Phe.OH, was used instead of N-Carbobenzoxy-L-prolyl-dehydrophenylalanyl-L-phenylalanine corresponded to 5% hydrolysis.

EXAMPLE 17

N-BOC-Leu-ΔPhe Azlactone

The dipeptide acid, BOC-Leu-Phe.OH (1.3 g, 3.47 mmol) is dissolved in dry tetrahydrofuran (20 ml) and dicyclohexylcarbodiimide (0.715 g, 3.47 mmol) is added. The resultant mixture is stored in a refrigerator overnight, the precipitated dicyclohexylurea is filtered off, and the filtrate is evaporated to give an amorphous, chromatographically pure azlactone: yield: 1.15 g (94%); which could not be crystallized; $R_f(E_4)$: 0.9; $R_f(Cr_3)$; 0.92. I.R. (film): $\nu_{max}=1842$ cm$^{-1}$.

2,3-Dichloro-5,6-dicyano-1,4-benzoquinone (0.7 g, 3.08 mmol) and collidine (0.37 g, 3.08 mmol) are added to a solution of the above azlactone (1.1. g, 3.08 mmol) in 1,2-dimethoxyethane (20 ml) and the mixture is stirred at room temperature for 3 days. The solvent is evaporated in vacuo and the dark brown residue is purified by passage through a silica gel column (30×2 cm) with 1:1 ether-petroleum ether as eluent. Recrystallization from ethyl acetate/pet. ether gave the unsaturated azlactone; yield: 490 mg (44%); m.p 128°–129°; $R_f$ (E$_4$): 0.94; $R_f$(CHCl$_3$): 0.81; $R_f$(ether): 0.56.

Anal. Calcd. for $C_{20}H_{26}N_2O_4$: C, 67.02; H, 7.31; N, 7.82. Found: 66.98; H, 7.36; N, 7.83. I.R. (nujol): $\nu_{max}=1805$, 1785, 1712 cm$^{-1}$. BOC=t-butoxy carbonyl.

EXAMPLE 18

S-Trityl-3-mercaptopropionic acid

A total of 10.61 g (0.1 mol) of 3-mercaptopropionic acid and 26.1 (0.11 mol) of triphenylcarbional was dissolved in 100 ml of glacial acetic acid at room temperature. To this solution was added 15.61 g of boron trifluoride etherate (0.11 mol) and the mixture was heated in a hot water bath. After 1 hour the acetic acid was removed in vacuo, and the resulting precipitate was recrystallized in DMF/H$_2$O giving 10.8 g (31.1%) of the desired product m.p. 217°–221°.

EXAMPLE 19

S-Trityl-3-Mercaptopropanoyl-L-proline

A solution of 1.51 g (0.01 mole) of L-proline in 20 mls of 2 N NaOH is chilled in an icebath and treated with a total of 4.03 g (0.011 mol) of S-trityl-3-mercaptopropionyl chloride and 20 ml of 2 N NaOH in 5 equal and alternate portions with vigorous intermittent shaking and cooling in an ice bath. The solution is kept at an alkaline pH by the addition of more alkali when necessary. Upon completion of the addition of the reagents, the reaction mixture is stirred for an additional 15 min. at room temperature and then acidified to Congo red with cooling by dropwise treatment with concentrated HCl. The reaction is placed in a refrigerator overnight. The resultant precipitate is recovered by filtration, washed several times with ice water and dried in a dessicator over phosphorus pentoxide. Recrystallization in EtOH/H$_2$O gave 3.2 g (72%) of the desired product. The NMR and IR showed the required peaks.

EXAMPLE 20

S-Trityl-3-mercaptopropanoyl-L-Prolyl-dl-Phenylalanine

A solution of 2.2 g (0.005 mol) of S-tritylated-3-mercaptopropanol-L-proline and 0.62 g (0.0052 mol) of N-methylmorpholine in 25 ml of dry tetrahydrofuran was cooled to around 0°, and 0.71 g (0.0052 mol) of isobutyl chloroformate in 10 ml of THF was added slowly. The reaction was stirred for 1 hr and a solution of 1.02 g (0.005 mol) of phenylalanine methyl ester hydrochloride in a mixture of 7 mls of dioxane and 3 mls of water, and a solution of 0.55 g (0.0052 mol) of triethylamine in 10 mls dioxane were added to the above solution and the reaction mixture was stirred overnight. The solution was extracted with ethyl acetate and the ethyl acetate was removed in vacuo. The resulting oil was dissolved in 10 ml of methanol and 10 ml of 1 N NaOH was added and stirred overnight. The reaction mixture was acidified to pH 3 with 4 N HCl. The oily product was extracted with ether, dried with anhyd. magnesium sulfate and the ether removed to give 1.86 g (63%) of the desired product. The NMR and IR showed the required peaks.

EXAMPLE 21

S-Trityl-3-mercaptopropanoyl-L-Prolyl-dl-Phenylalanine azlactone

A total of 0.6 g (0.001 mol) of S-trityl-3-mercaptopropanoyl-L-Prolyl-dl-Phenylalanine was dissolved in 25 mls of dry tetrahydrofuran. The solution is stirred at room temperature and 0.2 g (0.0011 mol) of N,N-dicyclohexylcarbodiimide was added. The solution stood in the refrigerator overnight and the total of 0.42 g (73.1%) of the desired product was obtained. The IR showed the characteristic carbonyl band for the azlactone.

EXAMPLE 22

S-Trityl-3-mercaptopropanoyl-L-Prolyl-dl-Phenylalanine Unsaturated Azlactone

A total of 0.4 g (0.007 mol) of the corresponding azlactone is dissolved in 20 mls of dry dimethoxyethane. A total of 0.008 g (0.00072 mol) of collidine, and 0.16 g (0.00072 mol) of 2,3-dichloro-5,6-dicyano-1,4-benzoquinone was then added to the solution, and the reaction mixture was stirred at room temperature for three days. The dimethoxyethane was removed in vacuo, and the resulting brown oil was eluted with ether/pet. ether (1:1) through 20 g of 60–200 mesh silica gel. Thin layer chromatography showed the product to be in the second and third 20 ml fractions. The solvents were removed and the resulting precipitate was recrystallized in ethyl acetate/hexane, to give 0.18 g (45%) of the unsaturated azlactone.

EXAMPLE 23

S-Trityl-3-Mercaptopropanoyl-Prolyl-Δ-Phenylalanyl-Histidyl-Leucine.OH

A total of 0.508 g (0.002 mol) and 0.23 g (0.002 mol) of 1,1,3,3-tetramethylguanidine were dissolved in a 24 of a 1.5 mixture of water and acetone. To this solution was added 1.14 g (0.002 mol) of S-trityl-3-mercaptopropanoyl-Prolyl-Δ-phenylalanine azlactone. The resulting mixture was refluxed 24 hours, water was added and the acetone was removed in vacuo. The residual aqueous solution was acidified with saturated citric acid to pH 3 and the separated oil was extracted into chloroform. The combined extracts were washed with water and dried over anhydrous $MgSO_4$. The solvent was evaporated in vacuo and the residual syrup was crystallized from chloroform-ether yielding 1.14 g (68%) of product.

EXAMPLE 24

3-Mercaptopropanoyl-Prolyl-dl-Phenylalanyl-Histidyl-Leucine

A total of 1.14 g of the protected tetrapeptide was dissolved in 20 mls of 80% acetic acid. The solution was heated at 50 degrees for 1 hour. The acetic acid was removed in vacuo. The solid triphenylcarbinol was removed from the peptide by washing with ether, to give a quantitative yield (0.8 g) of 3-mercaptopropanoyl-Prolyl-dl-phenylalanyl-histidyl-leucine.

EXAMPLE 25

N-carbobenzoxy-Gly-Gly-Phe azlactone

To a solution of 1.00 g (2.4 mmoles) of N-carbobenzoxy-gly-gly.Phe in 20 ml of absolute THF at 0° was added a cold solution of 0.495 g of DCC in 10 ml of THF. The mixture was allowed to stand at 0° for 24 hr. and was then filtered, avoiding moisture as much as possible. (Attempts to isolate the product were unsuccessful due to ease of hydrolysis to the starting acid.)

EXAMPLE 26

N-carbobenzoxy-Gly-Gly-ΔPhe-azlactone

To a cooled solution (0°) of 0.95 g (2.42 mmoles) of N-carbobenzoxy-gly-gly-phe azlactone in 15 ml. of freshly distilled DME was added 1 eq. (6.293 g, 0.268 ml) of collidine and 1 eq. (0.549 g) of dichlorodicyanoquinone dissolved in 10 ml of DME. The stirred mixture was allowed to warm to room temperature and after 48 hrs. the DME was removed in vacuo. The residue was dissolved in ethyl acetate and the solution was washed with saturated $NaHCO_3$ and saturated NaCL and dried over anhyd. $MgSO_4$. The crude N-carbobenzoxy-gly-gly-Δphe-azlactone was purified on a silica gel column (10 g) and recrystallized from ethyl acetate/pet. ether to give 0.20 g (22%) of product, m.p. 145°–147°; IR 3315 (N—H); 1800 (C═O, ring), 1700 (C═O), 1660 (C═O); NMR δ7.3 (m, Ar ring, vinyl protons, 5.15 (s, 2H, $CH_2Z$), 4.5 (d, $GH_2Gly$), 4.0 (d, $CH_2Gly$).

Anal. Calcd. for $C_{21}H_{19}N_3O_5$: C, 64.12; H, 4.87; N, 10.68. Found: C, 64.03; H, 4.90; N, 10.68.

EXAMPLE 27

N-carbobenzoxy-Gly-Gly-Phe-MetNH₂

To a solution of 55 mg. (0.14 mmoles) of N-carbobenzoxy-gly-gly-phe-azlactone in 10 ml of $CH_2Cl_2$ was added 0.040 g (0.28 mmoles) of methionine amide. The reaction was stirred at room temperature for 12 hrs., the $CH_2Cl_2$ was removed and the residue was dissolved in 20 ml of EtOAc. The solution was washed with 0.10 N HCl, dried via anhyd. $MgSO_4$, and concentrated. Addition of pet. ether promotes crystallization to yield 45 mg (60%) of N-carbobenzoxy-gly-gly-phe-$MetNH_2$ m.p. 155°–157°.

Anal. Calcd. for $C_{26}H_{31}N_5O_6S_1$: C, 57.66; H, 5.77; N, 12.93. Found: C, 57.86; H, 5.96; N, 12.83.

EXAMPLE 28

Tyr-DAla-GLy-ΔPhe-Met-NH₂ Acetate

To a solution of 0.75 g (1.4 mmoles) of 7 in 20 ml of DMF was added 1 eq. (0.14 g, 0.10 ml) of triethylamine and with stirring 1.05 eq. (0.55 g) of BOC-tyr-OSu. The reaction mixture was stirred overnight and the DMF was removed in vacuo. The residue was dissolved in EtOAc and the solution was washed with 5% citric acid, saturated $NaHCO_3$, and saturated NaCl solution, dried over anhydrous $MgSO_4$ and concentrated to 2 ml. The pentapeptide was precipitated by addition of diethyl ether, washed several times with fresh portions of ether, and the residual solvent was removed in vacuo a pale yellow solid, which, when treated with 10 ml of trifluoroacetic acid yielded 0.62 g of the trifluoroacetate salt. $R_f(D)=0.38$.

The crude trifluoroacetate salt was dissolved in 2 ml of 5% acetic acid solution and was then passed through an ion exchange column (50 ml) of the acetate form of Dowex 1-X4 ion exchange resin. The column was washed with 500 ml of 5% acetic acid solution and the resulting solution was concentrated to 2 ml and placed on a 65×1½ cm. column of Biogel $P_2$. The Biogel column was eluted with 5% acetic acid to yield 200 mg of the pure acetate salt after lyophilization; $[\alpha]_D^{27} = +31.6°$, (C=1, $H_2O$); $R_f$ (E)=0.19, $R_f$ (C)=0.81; amino acid analysis showed a 1.00:1.00:0.90:1.02 ratio of Tyr:Gly:Ala:Met.

Anal. Calcd. for $C_{30}H_{40}N_6O_8S_1.H_2O$: C, 54.43; H, 6.39; N, 12.69. Found: C, 54.42; H, 6.38; N, 12.71.

7=D-ala-Gly-ΔPhe-Met-NH₂ Trifluoroacetate.

EXAMPLE 29

BOC-DAla-Gly-ΔPhe-Met NH₂

To a cold solution (0°) of 0.534 g (2.58 mmoles) of BOC-D-alanine in 25 ml of DMF was added 0.582 g (2.82 mmoles) of DCC and 0.482 g (3.15 mmoles) of HOBt. After stirring for 15 min. a solution of 1.13 g of 4 and 0.189 ml of triethylamine in 10 ml of DMF was added. The reaction was stirred for 13 hours and was then filtered and the DMF was removed in vacuo. The residue was dissolved in 100 ml of EtOAc, filtered to remove dicyclohexyl urea, and the solution was washed with 5% citric acid, saturated $NaHCO_3$, and saturated NaCl solution. The solution was dried over anhydrous $MgSO_4$ and was concentrated to approximately 5 ml. The amorphous tetrapeptide was precipitated by addition of diethyl ether, washed several times with fresh ether, and dried in vacuo to yield 0.73 g (54% $R_f$ (A)=0.65, $R_f(B)=0.76$. Amino acid analysis indicates a ratio of Gly:Ala:Met of 1.09:0.98:0.93. (ΔPhe not present due to destruction during hydrolysis). $[\alpha]_D^{27°} = +54.1°$ (C=1, DMF).

EXAMPLE 30

D-Ala-Gly-ΔPhe-Met-NH₂ trifluoroacetate

A 0.7 g sample of the tetrapeptide BOC-D-Ala-Gly-ΔPhe-Met-NH₂ was treated at 0° with 10 ml of trifluoroacetic acid. After 15 min., 50 ml of anhyd. diethyl ether was added and the resulting solid precipitate was triturated thoroughly, washed with several portions of fresh ether, and collected. The residual solvent was removed in vacuo to yield 0.75 g of D-Ala-Gly-ΔPhe-Met-NH₂ trifluoroacetate, which was used immediately in the next coupling reaction.

EXAMPLE 31

Glycyl-dehydrophenylalanyl-methionine amide hydrobromide

Hydrogen bromide was bubbled into a solution of 1.00 g (2.06 mmoles) of 3 in 25 ml of glacial acetic acid. The addition of hydrogen bromide was stopped after 1–1.5 minutes and the solution was allowed to stand at room temperature for 30 min; after which, 100 ml of anhyd. diethyl ether was added to the reaction mixture. The precipitated peptide hydrobromide was washed several times with fresh ether and dried in vacuo to yield 0.90 g (99%) of 4, m.p. 153°–155° d.

3 = N-carbobenzoxy-Glycyl-dehydrophenylanyl-methionine amido.

EXAMPLE 32

N-CBZ-Glycyl-dehydrophenylalanyl-methionine amide

To a solution of 1.5 g (4.46 mmoles) of 2 in 30 ml of absolute THF, was added a solution of 0.823 g (4.46 mmoles) of methionine amide hydrochloride and 0.45 g (0.328 ml, 4.46 mmoles) of triethylamine in 10 ml of 1:1 dioxane/water. The reaction was allowed to proceed overnight, after which the ninhydrin positive spot due to met amide had disappeared on TLC ($R_f$(A)=0.32). The THF was then removed in vacuo, the residue dissolved in EtOAc, and the solution was washed with 1 N HCl, saturated KHCO₃, and saturated NaCl solution. After drying over anhyd. MgSO₄, the product crystallized from the cooled solution to yield 0.8 g (37%) of 3, m.p. 170°–172°; $[\alpha]_D^{29°} = +49.1°$ (C=1, DMF); $R_f$ (A)=0.57; IR (nujol) 3410 and 3300 (N—H), 1710, 1680, 1620 (C=O), 1640 cm⁻¹ (C=C); NMR (1:1 DMSO d₆/acetone d₆) δ7.8–7.2 (m, 14H, Ar—H, C=C—H), 5.2 (s, 2H, —CH₂—Ph), 4.0 (d, CH₂(gly)), 2.6 (m, —CH₂(met)), 2.1 (s, 3H, CH₃(met)), 2.2 (m, CH₂—(met)).

Anal. Calcd. for C₂₄H₂₈O₅N₄S₁: C, 59.49; H, 5.82; N, 11.56. Found: C, 59.52; H, 5.86; N, 11.52.

2 = N-carbobenzoxy glycyl-dehydrophenylalanine.

EXAMPLE 33

N-Benzyloxycarbonyl-S-benzyl-L-cysteinyl-O-benzyl-dehydrotyrosine azlactone

To 1.00 g (1.67 mmol) of N-benzyloxycarbonyl-S-benzyl-L-cysteinyl-O-benzyl-L-tyrosine in 10 ml of dry THF was added 0.35 g (1.67 mmol) of DCCl. The mixture was stirred overnight, cooled to 0° C. for 1 hr, filtered and the THF evaporated under reduced pressure to yield an oily residue. The oily residue was dissolved in 20 ml of DME and 0.202 g (1.67 mmol) of collidine and 0.379 g (1.67 mmol) of DDQ were added. The reaction mixture was stirred for 72 hrs. Silica gel (5 g) was added to the mixture and the DME was evaporated. The residue was removed and placed at the top of a 20 g silica gel column and eluted with 50:50 ether/pet. ether. Evaporation of the solvent yielded a yellow solid. The product was crystallized from methylene chloride/pet. ether to yield 0.5 g (51%). An analytical sample was obtained by elution with chloroform on a silica gel column and recrystallization twice from the same solvent pair: m.p. 135°–140°, ir (nujol) 1778 (C=O), 1680, (CONH), nmr (CDCl₃) δ2.20 (d 2H), 3.9 (s 2H), 5.4 (s, 4H, O—CH₂Ph), 6.9 (m, 1H, vinyl) 7.1–7.8 (m, 17H, ArH), 8.2 (m, 2H, ArH); $[\alpha]_D^{27}+7.6°$ (c, 1, CH₂Cl₂).

Anal. Calcd. for C₃₄H₃₀N₂O₅S₁: C, 70.56; H, 5.24; N, 4.84. Found: C, 70.32; H, 5.30; N, 4.81.

EXAMPLE 34

N-Benzyloxycarbonyl-L-prolyl-O-benzyl-dehydrotyrosine Azlactone

To a 50 ml roundbottom flask was added 2.0 g (4.0 mmol) of N-benzyloxycarbonyl-L-prolyl-O-benzyl-L-tyrosine and 20 ml of THF. The mixture was stirred for 1 hr. and 1.0 g (4.8 mmol) dicyclohexyl carbodiimide (DCCl) was added and the mixture was stirred at room temperature overnight. The mixture was cooled to 0° C. for 1 hr. and the dicyclohexylurea (DCU) was filtered. The filtrate was evaporated at reduced pressure to yield a yellow oil. The oil was dissolved in 20 ml of dimethoxyethane (DME) and 0.53 ml (4.0 mmol) of collidine and 0.91 g (4.0 mmol) of 2,3-dichloro-5,6-dicyano benzoquinone (DDQ) were added. The mixture was stirred for 72 hr. at room temperature. Silica gel (5 g.) was added to the reaction mixture and the DME was evaporated in vacuo. The solid residue was removed and placed at the top of a 20 g silica gel column and eluted with 1:1 ether/pet. ether. Evaporation of the solvent under reduced pressure yielded an oil from which the product was crystallized with methylene chloride/pet. ether. The yield was 0.67 g (35%). Two recrystallizations from the same solvent gave an analytical sample: mp 125°–127°, $$\text{ir (nujol) 1798 and 1775 } (-\overset{|}{\text{C}}=\text{O}),$$

1693, (CONH), 1648 cm⁻¹ (C=N); nmr (CDCl₃) δ2.18 (m, 4H, Pro ring), 3.60 (m, 2H, Pro ring), 4.85 (m, 1H, Pro ring), 5.15 (s, 4H, PhCH₂—), 6.70 (m, 1H, vinyl H), 6.8–7.6 (m, 12H, ArH), 8.1 ppm (d, 2H, ArH); $[\alpha]_D^{27} = 27.0°$ (c 1, CH₂Cl₂).

Anal. Calcd. for C₂₉H₂₆N₂O₅: C, 72.18; H, 5.43; N, 5.81. Found: C, 71.94; H, 5.46; N, 5.73.

EXAMPLE 35

N-Benzyloxycarbonyl-Phe-Δ-Phe Azlactone

To a cooled solution of ZPhePhe.OH (2.83 g, 6.6 mmol) in freshly distilled 1,2-dimethoxyethane (40 ml) is added 2,3-dichloro-5,6-dicyano-1,4-benzoquinone (1.5 g, 6.6 mmol) dissolved in dimethoxyethane (10 ml). After brief stirring, collidine (0.8 g, 0.734 ml, 6.6 mmol) is added. The mixture is stirred at room temperature and after 66 h the dimethoxyethane is removed in vacuo. The residue is dissolved in ethyl acetate and the solution is washed with saturated sodium hydrogen carbonate solution, saturated sodium chloride solution, and dried with anhydrous magnesium sulfate. The crude product is purified by chromatography on a column of silica gel (25 g) to give the pure product; yield: 0.9 g (33%); m.p. 168°–169°; $[\alpha]_D^{30}$: −65°±1° (c 1, DMF). I.R. (nujol): $\nu_{max}$=3310 (N—H), 1788 (C=O ring), 1700 (C—N), 1660 cm$^{-1}$ (C=O in benzyloxycarbonyl); H N.M.R. (CDCl$_3$): δ=7.3 (m, 15 H$_{arom}$); 8.0 (m, HN, 1H); 5.1 ppm (s, 2H, CO—O—CH$_2$C$_6$H$_5$).

Z=N-carbobenzoxy.

EXAMPLE 36

Z-Pro-ΔPhe-Arg(Tos)-O Resin

To a stirred slurry of 1 g of neutralized Arg-(Tos)-O Resin (0.5 mmole Arg) in 10 ml of DMF was added 1 g (2.65 mmole) Z-Pro-ΔPhe azlactone. After shaking for 24 hr the solution was filtered and a small sample of the collected resin was tested for complete reaction (ninhydrin test, E. Kaiser, et al., Anal. Biochem., 34, 595 [1970]). After washing 1×10 ml DMF and 5×10 ml CH$_2$Cl$_2$, the Z-Pro-ΔPhe-Arg (Tos)-O-resin was N-deblocked and used to complete the synthesis of ΔPhe$^8$ bradykinin.

Z=N-carbobenzoxy
Tos=Tosyl

I claim:

1. A method of preparing compounds represented by the formula (II)

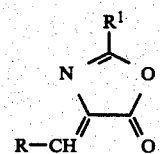

wherein
R is a straight- or branched-chain alkyl group of from 1 to 8 carbon atoms, which may be unsubstituted or substituted by hydroxyl, methylthio, guanidino or amino;
a phenyl or naphthyl group, which may be unsubstituted or substituted by hydroxyl, iodo or phenoxy; or
a 5-membered ring containing at least one nitrogen atom and at least 3 carbon atoms or a 5-membered ring containing one nitrogen atom and 4 carbon atoms fused to a benzene ring, which may be unsubstituted or substituted by hydroxyl; and
R$^1$ is an N-blocked amino acid residue or peptide chain or stereoisomer thereof; which comprises reacting a compound represented by the formula (I)

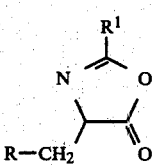

wherein
R and R$^1$ are as defined above in an organic solvent with a benzoquinone oxidizing agent in the presence of a base having a pK of about 6 to 8 and recovering the product.

2. The method according to claim 1, wherein the oxidizing agent is selected from the group consisting of 2,3-dichloro-5,6-dicyano-p-benzoquinone, σ-chloranil, p-chloranil and diphenoquinone.

3. The method according to claim 1 or 2, wherein the base is selected from the group consisting of collidine, pyridine and imidazole.

4. The method according to claim 3, wherein the base is collidine.

5. A compound represented by the formula (III)

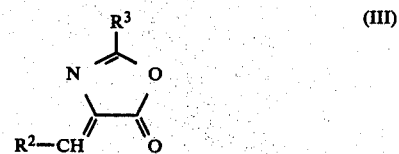

wherein
R$^2$ is phenyl; and
R$^3$ is an N-blocked amino acid residue selected from the group consisting of aspartic acid, glycine, leucine, proline and stereoisomers thereof.

6. The compound according to claim 5, wherein R$^3$ is an N-carbobenzoxy-prolyl group.

7. The compound according to claim 5, wherein R$^3$ is an N-carbobenzoxy-leucyl group.

8. The compound according to claim 5, wherein R$^3$ is an N-carbobenzoxy-aspartyl group.

9. The compound according to claim 5, wherein R$^3$ is an N-t-butoxycarbonyl-leucyl group.

10. The compound according to claim 5, wherein R$^3$ is an N-carbobenzoxy-glycyl group.

* * * * *

UNITED STATES PATENT AND TRADEMARK OFFICE
CERTIFICATE OF CORRECTION

PATENT NO. : 4,350,628

DATED : September 21, 1982

INVENTOR(S) : CHARLES H. STAMMER

It is certified that error appears in the above—identified patent and that said Letters Patent is hereby corrected as shown below:

Column 2, line 31, delete "tyrosylglycyl-glycyl dehydrophenylalanyl" and insert --tyrosyl-glycyl-glycyl-dehydro-phenylalanyl--.

Column 4, line 60, delete "PHENYLALNINE" and insert --PHENYLALANINE--.

Column 6, line 4, delete "as" and insert --are--; and line 44, delete "tryptohan" and insert --tryptophan--.

Column 7, line 38, delete "dehydro-histi-" and insert --dehydrohisti- --.

Column 8, line 14, delete "enkapha-" and insert --enkepha- --.

Column 9, line 8, delete "HOAC" and insert --HOAc--.

Column 11, line 44, after "Pro ring", insert --)-- (close parenthesis); and line 61, delete "N-hydrochol-" and insert --N-hydrochl- --.

UNITED STATES PATENT AND TRADEMARK OFFICE
CERTIFICATE OF CORRECTION

PATENT NO. : 4,350,628
DATED : September 21, 1982
INVENTOR(S) : CHARLES H. STAMMER Page 2 of 6

It is certified that error appears in the above—identified patent and that said Letters Patent is hereby corrected as shown below:

Column 12, line 17, delete " N carboben-" and insert --N-carboben- --;

line 21, delete "precipitated"; and line 47, delete "Acetone" and insert --acetone--.

Column 13, line 28, delete "exchang" and insert --exchanged--; and line 57, delete "8.0-8.27" and insert --8.0-8.2--.

Column 14, line 26, after "Pro ring" (second occurrence), insert --)-- (close parenthesis);

line 31, delete "5,03" and insert --5.03--;

line 36, delete "dehydrohpenylalanine" and insert --dehydrophenylalanine--;

line 40, delete "L-prolyldehydro-" and insert --L-prolyl-dehydro- --; and line 64, delete "ylcarbodiimid" and insert --ylcarbodiimide--.

UNITED STATES PATENT AND TRADEMARK OFFICE
CERTIFICATE OF CORRECTION

PATENT NO. : 4,350,628

DATED : September 21, 1982

INVENTOR(S) : CHARLES H. STAMMER

Page 3 of 6

It is certified that error appears in the above—identified patent and that said Letters Patent is hereby corrected as shown below:

Column 15, line 13, delete "N-Carbobenzoxyglyclydehydrophenylalanine" and insert --N-Carbobenzoxyglycyldehydrophenylalanine--;

line 15, delete "Mmole" and insert --mmole--;

line 24, delete "zlactone" and insert --azlactone--;

still line 24, delete "N-arbobenzoxyglycyldehydro-" and insert --N-carbobenzoxyglycyldehydro- --;

line 34, delete "N-Carbobenzoxyglyclydehydrophenylalanine" and insert --N-Carbobenzoxyglycyldehydrophenylalanine--;

line 36, delete "N-carbobenzoxyglyclydehydrophenylalanine" and insert --N-carbobenzoxyglycyldehydrophenylalanine--;

line 41, delete "zoxyglyclydehydrophenylalanine" and insert --zoxyglycyldehydrophenylalanine--;

line 47, delete "Glyclydehydrophenylalanine" and insert --Glycyldehydrophenylalanine--;

UNITED STATES PATENT AND TRADEMARK OFFICE
CERTIFICATE OF CORRECTION

PATENT NO. : 4,350,628
DATED : September 21, 1982
INVENTOR(S) : CHARLES H. STAMMER Page 4 of 6

It is certified that error appears in the above—identified patent and that said Letters Patent is hereby corrected as shown below:

line 51, delete "zoxyglyclydehydrophenylalanine" and insert --zoxyglycyldehydrophenylalanine--;

line 57, delete "Glyclydehydrophenylalanine" and insert --Glycyldehydrophenylalanine--; and line 67, delete "clydehydrophenylalanine" and insert --cyldehydrophenylalanine--.

Column 16, line 8, delete "Glyclydehydro-" and insert --Glycyldehydro- --;

line 15, delete "N-carbobenzoxyglyclydehydrophenyl-alanine" and insert --N-carbobenzoxyglycyldehydrophenylalanine--;

line 28, delete "clydehydrophenylalanine" and insert --cyldehydrophenylalanine--; and line 31, delete "glyclydehydrophenylalanine" and insert --glycyldehydrophenylalanine--.

Column 17, line 35, delete "amprphous" and insert --amorphous--;

line 37, delete "$[\alpha]_D^{32}$" and insert --$[\alpha]_D^{22}$--; and

UNITED STATES PATENT AND TRADEMARK OFFICE
CERTIFICATE OF CORRECTION

PATENT NO. : 4,350,628
DATED : September 21, 1982
INVENTOR(S) : CHARLES H. STAMMER It is certified that error appears in the above—identified patent and that said Letters Patent is hereby corrected as shown below:

line 66, delete "evaporate" and insert --evaporated--.

Column 18, line 6, delete "or" and insert --of--; and line 32, delete "yielded" and insert -- Yields --.

Column 19, line 62, delete "icebath" and insert --ice bath--.

Column 20, line 16, delete "captopropanol" and insert --captopropanoyl--;

line 55, delete "0.007" and insert --0.0007--.

Column 21, line 6, delete "tetramethylquanidine" and insert --tetramethylguanidine--;

still line 6, after "24", insert --ml--;

line 7, delete "1.5" and insert --1:5--; and line 59, after "protons", insert --)-- (close parenthesis)

Column 22, line 13, delete "GLy" and insert --Gly--; and

UNITED STATES PATENT AND TRADEMARK OFFICE
CERTIFICATE OF CORRECTION

PATENT NO. : 4,350,628

DATED : September 21, 1982

INVENTOR(S) : CHARLES H. STAMMER

It is certified that error appears in the above—identified patent and that said Letters Patent is hereby corrected as shown below:

line 64, after "(54%", insert --)-- (close parenthesis).

Column 23, line 27, delete "amido" and insert --amide--.

Signed and Sealed this

Twelfth Day of April 1983

[SEAL]

Attest:

Attesting Officer

GERALD J. MOSSINGHOFF

Commissioner of Patents and Trademarks